(12) United States Patent
Peyman et al.

(10) Patent No.: US 6,197,057 B1
(45) Date of Patent: Mar. 6, 2001

(54) LENS CONVERSION SYSTEM FOR TELEDIOPTIC OR DIFRACTIVE CONFIGURATIONS

(76) Inventors: Gholam A. Peyman, 8654 Pontchartrain Blvd., Unit 1, New Orleans, LA (US) 70124; Jeffrey E. Koziol, S. Dogwood, Rolling Meadows, IL (US) 60068

( * ) Notice: Subject to any disclaimer, the term of this patent is extended or adjusted under 35 U.S.C. 154(b) by 0 days.

(21) Appl. No.: 09/178,739

(22) Filed: Oct. 27, 1998

(51) Int. Cl.[7] .......................................................... A61F 2/16
(52) U.S. Cl. .......................... 623/6.32; 623/6.33; 623/6.34
(58) Field of Search ................................. 623/6.31, 6.32, 623/6.33, 6.34, 6.35, 6.11, 6.23, 6.25, 6.26

(56) References Cited

U.S. PATENT DOCUMENTS

| | | |
|---|---|---|
| 4,581,031 | 4/1986 | Koziol et al. . |
| 4,666,446 | 5/1987 | Koziol et al. . |
| 4,932,971 | 6/1990 | Kelman . |
| 5,098,444 | 3/1992 | Feaster . |
| 5,358,520 | 10/1994 | Patel . |
| 5,366,502 | 11/1994 | Patel . |

FOREIGN PATENT DOCUMENTS

| WO 9407435 | 4/1994 | (WO) . |
|---|---|---|

*Primary Examiner*—Mickey Yu
*Assistant Examiner*—Dinh X. Nguyen
(74) *Attorney, Agent, or Firm*—Roylance, Abrams, Berdo & Goodman, L.L.P.

(57) ABSTRACT

A supplemental intraocular lens is provided for implantation in the eye to modify the lens system of the eye comprising the cornea and the natural lens or an intraocular lens already implanted in the eye, to create a modified lens system having teledioptic or other diffractive capabilities to correct for macular degeneration. To create the teledioptic lens system, the supplemental intraocular lens has substantially no refractive power except for a high minus lens portion at its center. The supplemental intraocular lens, when implanted on the natural or previously implanted artificial lens in the eye and used without an external lens, allows light rays entering the eye onto the retina of the eye as they would without the supplemental intraocular lens, thus providing unmagnified and peripherally unrestricted vision. When a spectacle lens is placed in front of the cornea, the spectacle lens, cornea, natural or intraocular lens and supplemental intraocular lens provide the eye with magnified and restricted peripheral vision. To create a lens system having other diffractive capabilities, a light diffractive supplemental intraocular lens, such as a prism-shaped intraocular lens, having no refractive power is implanted in the eye. The prism-shaped supplemental intraocular lens, the natural lens or artificial lens already implanted in the eye, and the cornea of the eye create a lens system which redirects the light rays entering the eye onto a portion of the retina away from the macula to create an image unaffected by macula degeneration.

30 Claims, 14 Drawing Sheets

NATURAL EYE & SUPPLEMENTAL IOL

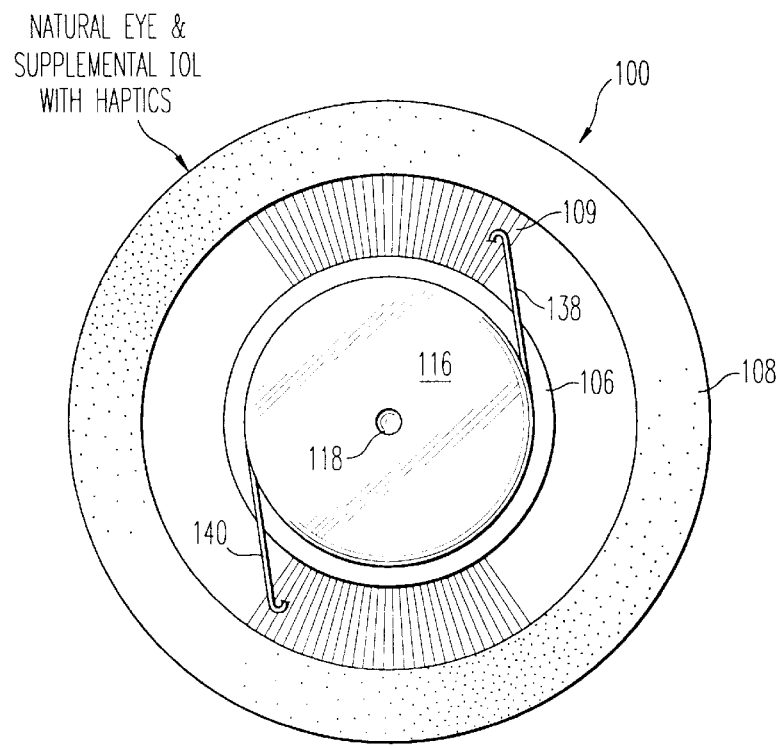
FIG. 12
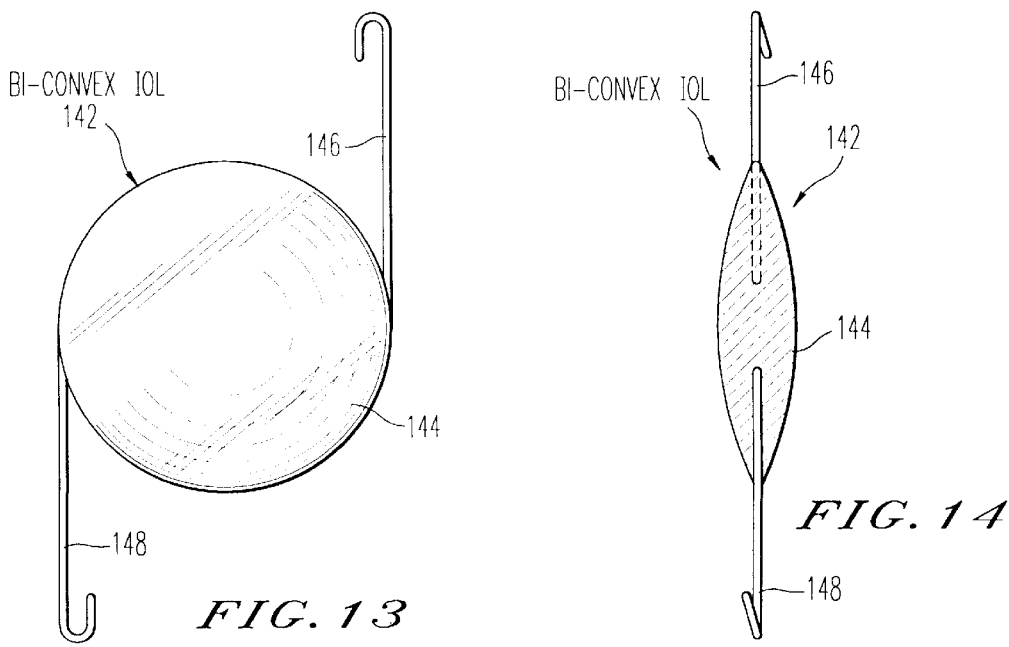
FIG. 13
FIG. 14

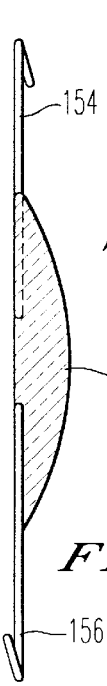
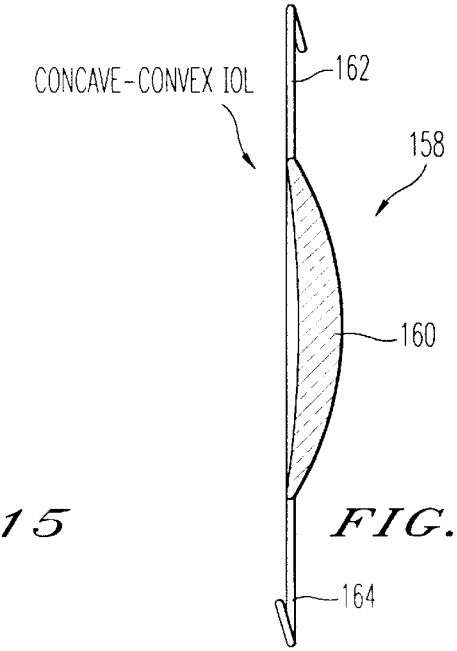
FIG. 15    FIG. 16
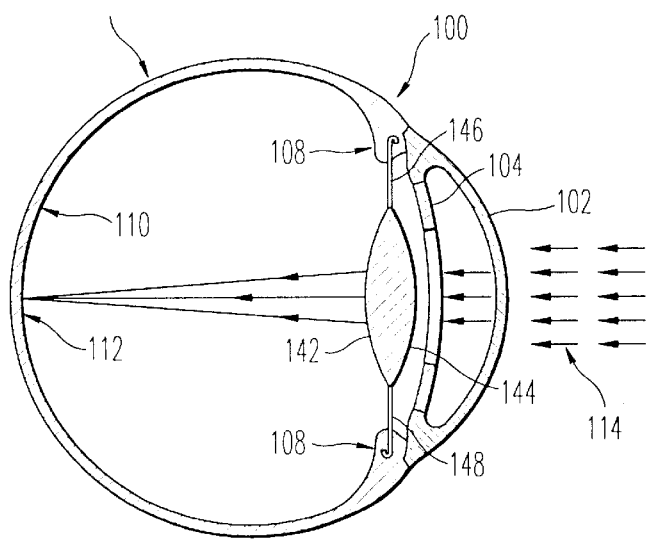
FIG. 17

LENS CONVERSION SYSTEM FOR TELEDIOPTIC OR DIFRACTIVE CONFIGURATIONS

BACKGROUND OF THE INVENTION

1. Field of the Invention

The present invention relates to intraocular lenses to be implanted onto a natural or artificial lens in the eye to modify the existing lens system of the eye comprising the cornea and a natural or existing artificial lens. More particularly, the invention relates to an intraocular lens having either a substantially non-refractive configuration with a high minus portion at its center, or a substantially non-refractive prismatic or other diffractive configuration, and which is adaptable for implantation in the eye to modify the natural lens or an existing artificial lens to be adaptable to function as a teledioptic lens or diffractive lens, respectively.

2. Description of the Related Art

A normal ametropic eye includes a cornea, lens and retina. The cornea and lens of the normal eye cooperatively focus light entering the eye from a far point, i.e., infinity, onto the retina. However, an eye can have a disease known as macular degeneration which can greatly degrade vision.

Macular degeneration has become one of the leading causes of blindness in adults. This disease affects the central retinal area known as the macula which receives light focused by the cornea and lens and acute vision. Macular degeneration can lead to a gradual or sudden loss of vision to the level of 20/200 or less. Commonly, loss of vision only affects the central retinal area of about 0.25 to 4 square millimeters, and does not usually progress beyond this area, thereby leaving 95–99% of the retina unaffected. Thus, reading and driving vision can be lost, while peripheral vision remains intact.

U.S. Pat. Nos. 4,666,446 and 4,581,031, both to Koziol and Peyman, and both of which are incorporated by reference herein, each disclose intraocular lenses which are implanted in the eye in place of the natural lens to redirect the rays of light to minimize the adverse affect on vision caused by the macular degeneration of the eye. For example, U.S. Pat. No. 4,666,446 discloses an intraocular lens comprising a first portion including a diverging lens and a second portion including a converging lens. The converging lens provides the eye with substantially the same focusing ability of the natural lens prior to implantation of the intraocular lens. Thus, the eye will have decreased visual acuity due to the macular degeneration, but will also have unrestricted peripheral vision. The diverging lens, on the other hand, when combined with a converging lens positioned outside of the eye (e.g., a spectacle lens), provides a magnified image with increased visual acuity but a restricted visual field. Therefore, this type of intraocular lens creates teledioptic lens system, which provides the patient with the choice of unmagnified but peripherally unrestricted vision or magnified but peripherally restricted vision.

U.S. Pat. No. 4,581,031, discloses an intraocular lens including a convex portion and a prismatic portion. The combined convex/prismatic lens directs rays of light away from the center of the retina that has been damaged by macular degeneration, and focuses those rays onto an undiseased area of the retina, thus providing greater visual acuity.

As discussed above, U.S. Pat. Nos. 4,666,446 and 4,581,031 clearly disclose that it is known to use particular types of intraocular lenses in place of the natural lens to reduce the adverse affect of macular degeneration on vision. However, neither of the patents disclose that it is known to use an intraocular lens to modify an existing lens system in the eye, comprising the cornea and a natural or artificial lens already present in the eye, to create a lens system having the prismatic or teledioptic capabilities discussed above to correct for macular degeneration in the eye.

U.S. Pat. Nos. 5,098,444, 5,366,502, 5,358,520, and 4,932,971, as well as world patent application WO 94/07435, each disclose that it is known to attach a supplemental intraocular lens to an existing artificial intraocular lens to correct for ongoing degradation of vision. That is, if the ability of the eye to focus grows worse over time, instead of replacing the entire intraocular lens with a new intraocular lens having a different refractive power, a supplemental intraocular lens can be attached to the existing intraocular lens. This technique is less invasive and hence, less traumatic to the eye.

However, like U.S. Pat. Nos. 4,666,446 and 4,581,031, none of these patents discloses a supplemental intraocular lens that can be attached to the natural lens or an existing artificial lens to make the lens adaptable to function as a teledioptic or diffractive prismatic lens of the type described above. Accordingly, a continuing need exists for a supplemental intraocular lens having these capabilities.

SUMMARY OF THE INVENTION

An object of the invention is to provide a supplemental intraocular lens for modifying the natural lens of an existing artificial lens in an eye to correct for macular degeneration.

Another object of the present invention is to provide an intraocular lens for implantation in the eye to modify the lens system of the eye comprising the cornea and the natural or existing artificial lens in the eye, to create a lens system that functions as a teledioptic lens system which, when used without an external lens, provides unmagnified and peripherally unrestricted vision and which, when used with an external lens, provides magnified and peripherally restricted vision to correct for macular degeneration.

Another object of the invention is to provide an intraocular lens for implantation in the eye to modify the lens system of the eye comprising the cornea and the natural or an existing artificial lens in the eye to create a lens system which redirects rays of light away from a diseased portion of the retina in the eye and focuses those rays onto an undiseased area of the retina.

A further object of the invention is to provide intraocular lenses of the types described above which further include fastening members which enable those intraocular lenses to be secured in the eye.

A still further object of the invention is to provide intraocular lenses of the type described above which are capable of being secured directly to the surface of the natural or existing artificial lens in the eye.

These and other objects of the invention are achieved by providing a supplemental intraocular lens which is substantially non-refractive except for a high minus portion at its center. The supplemental intraocular lens is adaptable for implantation in the eye in addition to the natural lens or an artificial lens already present in the eye. The intraocular lens modifies the lens system of the eye, comprising the cornea and the natural or existing artificial lens in the eye, to be adaptable to act as a teledioptic lens system. Specifically, the supplemental intraocular lens provides substantially no refractive power when used without an external lens, thus providing unmagnified and unrestricted peripheral vision.

On the other hand, when combined with a converging lens positioned outside of the eye, the high minus portion of the supplemental intraocular lens diverges the converging rays of the light and projects the diverging rays onto an area of the retina to provide a magnified image with a peripherally restricted field of view.

These and other objects are further achieved by providing an intraocular lens having a prism-shaped or other diffractive portion with substantially no refractive power. The intraocular lens of this type is inserted in the eye to modify the existing lens system of the eye, comprising the cornea and the natural or an existing artificial lens in the eye, to create a modified lens system that directs the rays of light entering the eye onto a portion of the retina different from that onto which the rays are directed without the prism-shaped intraocular lens. In particular, the rays are directed to a portion of the retina not damaged by macular degeneration.

The prism-shaped intraocular lens, as well as the teledioptic intraocular lens, each can be attached directly to the natural or artificial lens already in the eye and secured by an adhesive, or can each include fastening members, such as haptics, which secure the intraocular lenses to the eye.

BRIEF DESCRIPTION OF THE DRAWINGS

These and other objects and advantages of the present invention will be more readily appreciated from the following detailed description taken in conjunction with the accompanying drawings, in which:

FIG. 12 is a cross-sectional view taken through the eye directly behind the iris to further illustrate the supplemental intraocular lens having haptics as mounted to the natural lens of the eye as shown in FIG. 11;

FIG. 13 is a front view of an intraocular lens configured for implantation into an eye in place of the natural lens of the eye;

FIG. 14 is a cross-sectional view of the intraocular lens shown in FIG. 13 which is configured as a bi-convex lens;

FIG. 15 is a cross-sectional view of an alternate configuration of an intraocular lens of the type shown in FIG. 13, which has been configured as a plano-convex lens;

FIG. 16 is a cross-sectional view of another alternate configuration of the intraocular lens shown in FIG. 13, with the intraocular lens being configured as a concave-convex intraocular lens;

FIG. 17 is a cross-sectional view of an eye into which has been inserted a bi-convex intraocular lens;

DETAILED DESCRIPTION OF THE PREFERRED EMBODIMENTS

Figure 1:
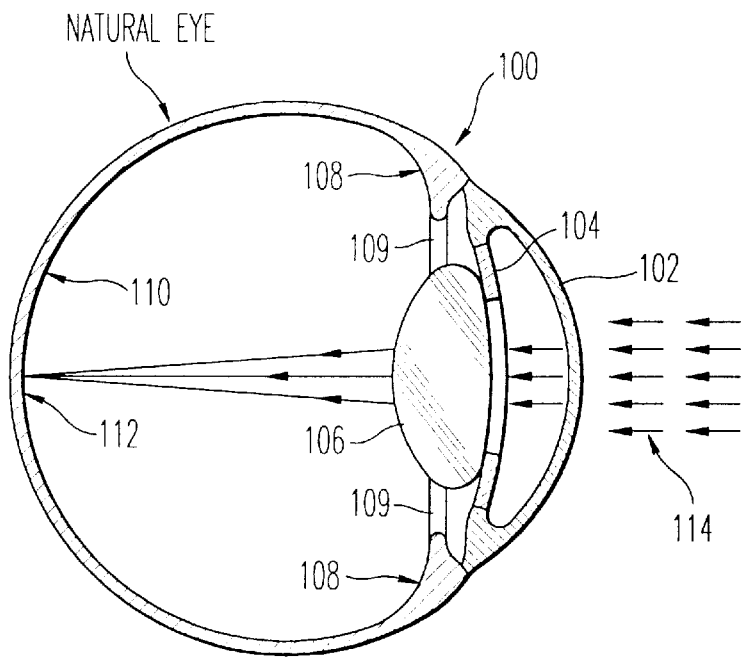
FIG. 1 is a cross-sectional view of a normal ametropic eye illustrating, among other things, the cornea, iris and lens of the eye.

FIG. 1 is a cross-sectional view of a normal ametropic eye 100. The eye 100 includes a cornea 102, an iris 104, a lens 106, a ciliary sulcus 108 adjacent the lens 106, a zonular ligament 109, a retina 110 and a macula 112. As illustrated, the macula 112 is located at the center of the retina 110 and is responsible for providing acute vision, such as that necessary for driving or reading.

As shown in FIG. 1, light rays 114 are focused directly on the macula 112 by the cornea 102 and lens 106. The cornea 102 has, on the average, 40 diopters of plus power, and the lens has 20 diopters of plus power. The combination of the cornea 102 and lens 106 therefore is equivalent to a very strong lens of 60 diopters. The light rays 114 which enter the eye in a direction perpendicular or substantially perpendicular to the front surface of the cornea 102 are focused on the macula 112 and provide acute vision. The light rays 114 striking the cornea 102 obliquely are unfocused and provide peripheral, less acute vision.

When macula degeneration exists, visual acuity is decreased, which results in a blurred spot in the center of vision. However, the less acute peripheral vision remains substantially the same as in an eye not suffering from macula degeneration.

As discussed in the background section above, in an eye suffering from macula degeneration, a portion of the retina is damaged. The damaged portion of the retina does not sufficiently detect the light rays being focused on that portion by the cornea 102 and lens 106. Therefore, the person perceives an image with low visual acuity.

As further discussed above, the adverse affect of the macula degeneration can be minimized by using a teledioptic lens having a convex lens portion and a concave lens portion as described in U.S. Pat. No. 4,666,446. However, instead of replacing the natural lens 106 with that type of teledioptic lens, the existing lens system of the eye comprising the cornea 102 and natural lens 106 can be converted into a modified lens system having the teledioptic described above, through the use of a supplemental intraocular lens according to the present invention as shown, for example, in FIGS. 2 and 3.

Figure 2:
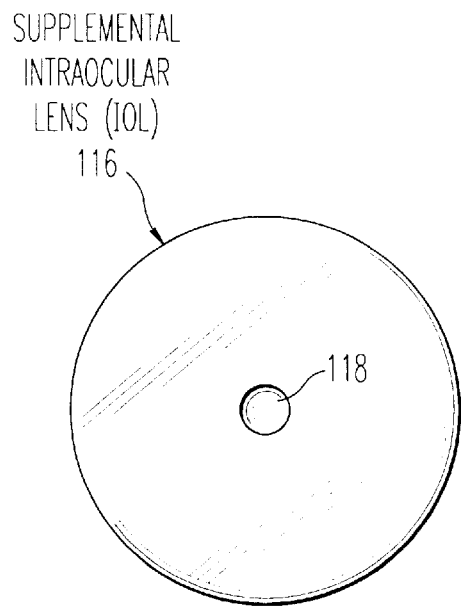
FIG. 2 is a front view of an example of a bi-concave supplemental intraocular lens according to an embodiment of the present invention, which is substantially non-refractive except for a high minus portion at its center, and is used to convert the natural lens or an existing artificial lens in the eye into a lens having teledioptic capabilities.
Figure 3:
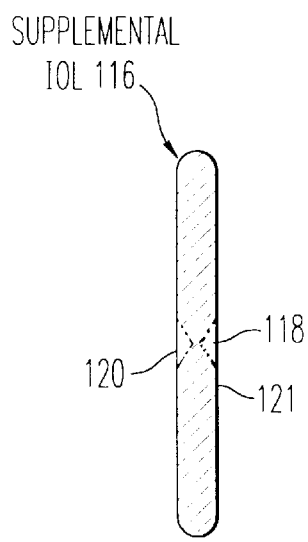
FIG. 3 is a cross-sectional view of a bi-concave supplemental intraocular lens as shown in FIG. 2.

FIGS. 2 and 3 are front and side views, respectively, of a bi-concave supplemental intraocular lens 116 according to an embodiment of the present invention. The supplemental intraocular lens 116 is made of a flexible synthetic transparent material, organic transparent material, or a combination of both. Suitable materials are collagen, copolymer collagen, polyethylene oxide or hydrogel, hyaluric acid, mucopolysaacharide or glycoprotein, to name a few.

The bi-concave supplemental intraocular lens 116 has, for example, planar or substantially planar surfaces having recessed portions 118 and 120 therein, which are each circular or substantially circular in shape and have a central axis equal to or substantially equal to the central axis of the supplemental intraocular lens 116. These recessed portions 118 are typically about 1 millimeter to about 3 millimeters in diameter, and the overall diameter of the supplemental intraocular lens 116 can range between about 3 millimeters and about 10 millimeters. The recessed portions 118 and 120 act as a minus lens having a power ranging between −30 diopters to about −120 diopters depending on the diameter of the recessed portion, the thickness of the supplemental intraocular lens 116, and the shape and depth of the recessed portions 118 and 120. However, the remainder of the supplemental intraocular lens 116 has no or substantially no refractive power.

Figure 4:
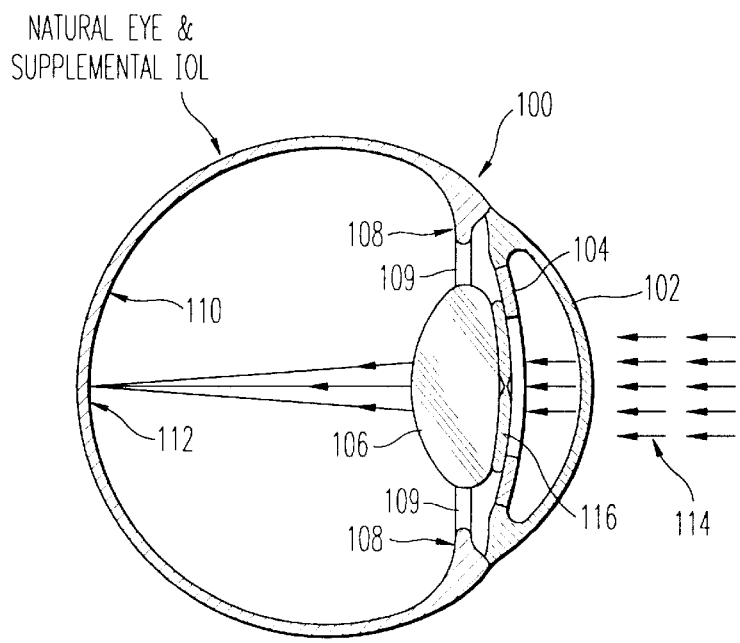
FIG. 4 is a cross-sectional view of an eye having a bi-concave supplemental intraocular lens as shown in FIG. 2 positioned on the natural lens of the eye.
Figure 5:
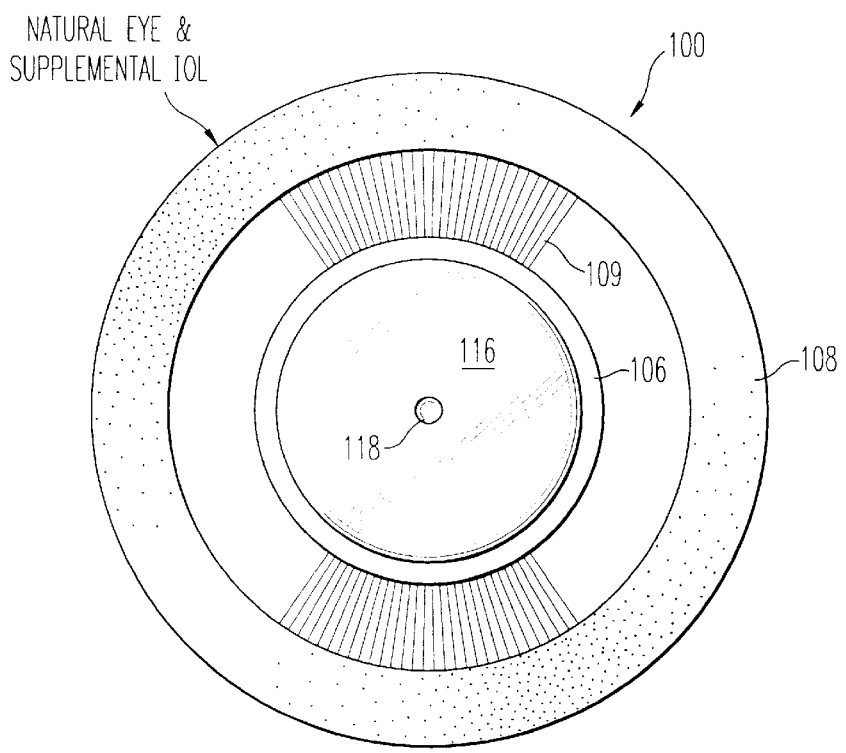
FIG. 5 is a cross-sectional view taken through the eye directly behind the iris to further illustrate the supplemental intraocular lens positioned on the natural lens of the eye as shown in FIG. 4.

To implant the supplemental intraocular lens in the eye, an incision is made in the eye through the use of a microkeratome, laser or other suitable surgical device. One side of the supplemental intraocular lens 116 can be coated with glue or any other suitable adhesive. As shown in FIGS. 4 and 5, the supplemental intraocular lens 116 is attached directly to the natural lens 106 and is positioned centrally or substantially centrally on the lens 106. Accordingly, this modified lens system comprising the cornea 102, the natural lens 106 and the supplemental intraocular lens 116 functions as a teledioptic lens as described in U.S. Pat. No. 4,666,446.

That is, as shown in FIG. 4, the light rays 114 entering the eye are focused by the cornea 102, the natural lens 106 and the supplemental intraocular lens 116 onto an area of the retina 110. However, since the supplemental intraocular lens 116 has no refractive power (except for recessed portions 118 and 120), the light rays 114 are focused on the same or substantially the same area of the retina that the lens 103 and cornea 102 focus the rays without the supplemental intraocular lens 116. Hence, this modified lens system will provide the person with virtually the same unmagnified vision and unrestricted peripheral vision that is provided without the supplemental intraocular lens 116.

Figure 6:
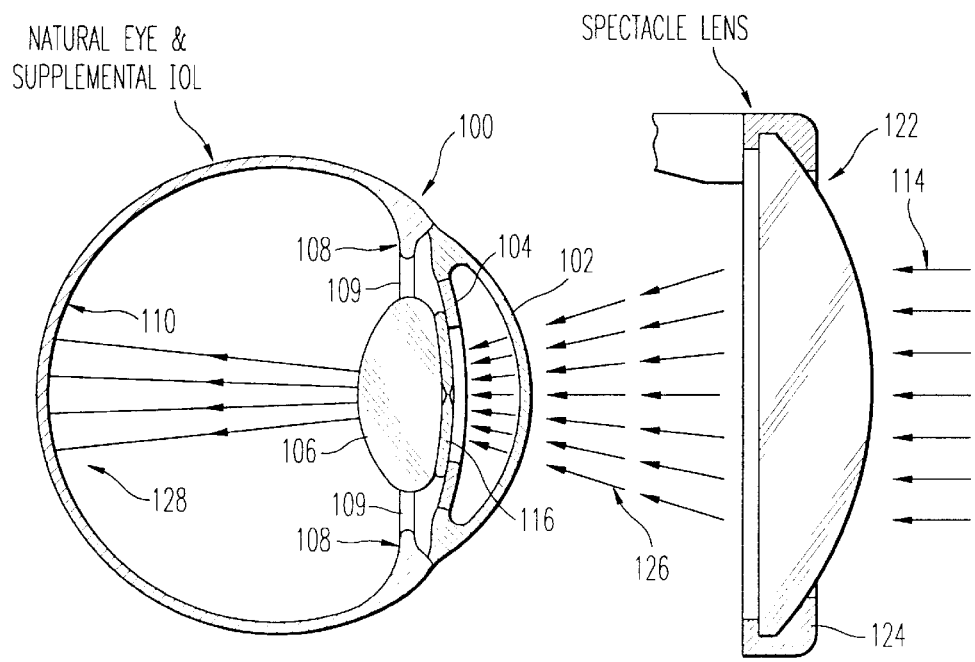
FIG. 6 is a cross-sectional view of an eye into which has been implanted a bi-concave supplemental intraocular lens as shown in FIG. 4, and with which a spectacle lens is being used.

However, as shown in FIG. 6, a spectacle lens 122, which is, for example, mounted in a spectacle frame 124, can be placed in front of the eye 100 in which a supplemental intraocular lens 116 has been implanted. In this example, the spectacle lens 122 is a converging lens which causes the light rays 114 to converge as converging light rays 126 which strike the cornea 102 of the eye at a certain angle of convergence relative to the optical axis of the eye 100. These converging light rays 126 pass through the cornea 102 and then through the lens 106 and the supplemental intraocular lens 116.

The high minus portion (i.e., recessed portions 118 and 120) of the supplemental intraocular lens 116 acts as a diverging lens system which causes the converging light rays 126 to diverge to produce a magnified retinal image 128 on the retina 110. This combination of a converging spectacle lens 122 and diverging lens system comprising natural lens 106 and supplemental intraocular lens 116 is known as a Galilean telescope.

As stated above, recessed portions 118 and 120 of the supplemental intraocular lens 116 provide a high minus lens having a refractive power from about −40 diopter to about −120 diopter, but can have any power suitable for this application. The converging spectacle lens will normally have a power from about +25 diopter to about +35 diopter, but can have any power suitable for this application. The magnification provided by this combination of a spectacle lens 122 and supplemental intraocular lens 116 can range from about 2× to about 4×, depending on the power and vertex distance of the spectacle lens 122. The field of vision will also range from about 35° to about 45°, depending upon the selected magnification.

Figure 7:
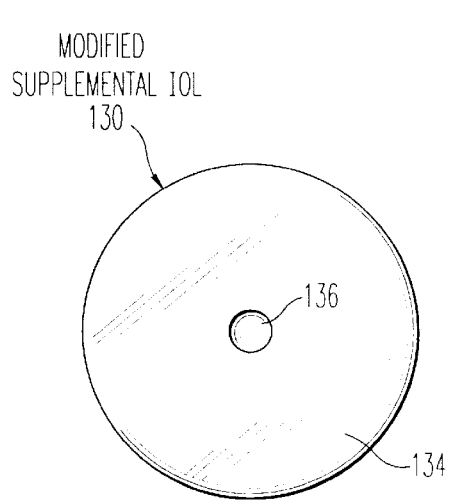
FIG. 7 is a front view of a plano-concave supplemental intraocular lens according to an embodiment of the present invention, which is substantially non-refractive except for a high minus portion at its center, and which is used to convert the natural lens or an existing artificial lens in the eye into a lens having teledioptic capabilities.
Figure 8:
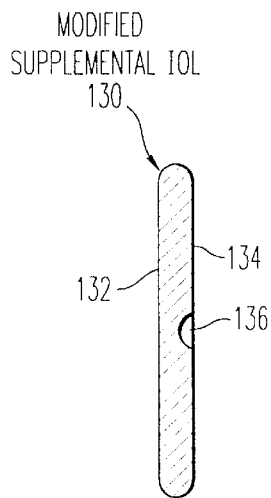
FIG. 8 is a cross-sectional view of the plano-concave supplemental intraocular lens as shown in FIG. 7.

The supplemental intraocular lens also can have shapes other than bi-concave. For example, as shown in FIGS. 7 and 8, the supplemental intraocular lens 130 according to another embodiment of the invention is plano-concave, and has a planar side 132 and a recessed side 134 having a recessed portion 136 therein. Like supplemental intraocular lens 116, supplemental intraocular lens 130 has substantially no refractive power except for at the recessed portion 136 which provides a high minus lens as described above. Accordingly, supplemental intraocular lens 130 can be used in a manner similar to that described above with regard to supplemental intraocular lens 116.

That is, supplemental intraocular lens 130 can be placed directly on the surface of a natural lens 106 of the eye 100 in a manner similar to that shown in FIGS. 4 and 5 which pertain to supplemental intraocular lens 116. Furthermore, a spectacle lens 122, as shown in FIG. 6, can be used in conjunction with the supplemental intraocular lens 130 to provide a magnified retinal image similar to magnified retinal image 128 as provided by supplemental intraocular lens 116. Like supplemental intraocular lens 116, supplemental intraocular lens 130 can be made of flexible synthetic transparent material, organic transparent material or both as described above. The minus lens formed by recessed portion 136 of supplemental intraocular lens 130 can be within the range of about −30 diopters to about −120 diopters.

Figure 9:
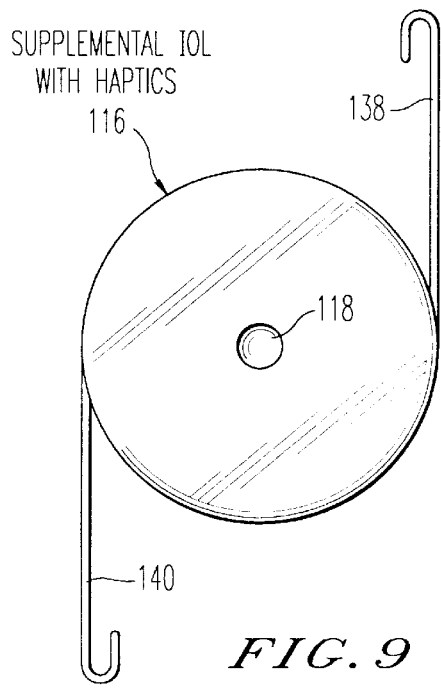
FIG. 9 is a front view of a bi-concave supplemental intraocular lens as shown in FIG. 2, having a pair of haptics for securing the supplemental bi-concave intraocular lens into the eye.
Figure 10:
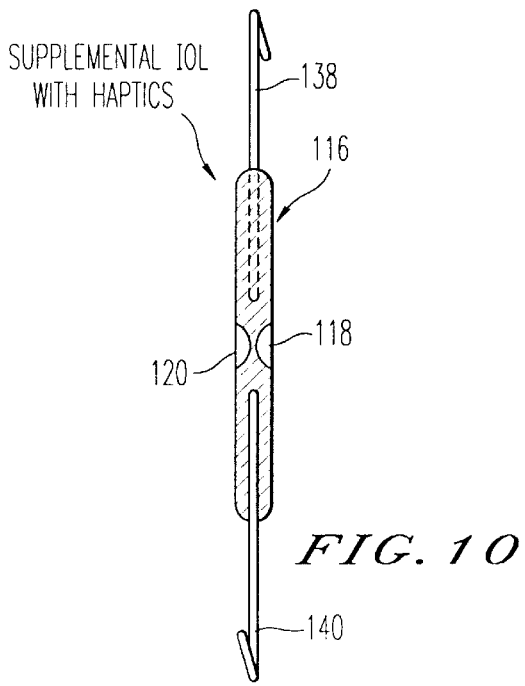
FIG. 10 is a cross-sectional view of a bi-concave intraocular lens as shown in FIG. 9.

Although the supplemental intraocular lens is shown as being either a bi-concave supplemental intraocular lens 116 or a plano-concave supplemental intraocular lens 130, the supplemental intraocular lens according to the present invention can any suitable shape, as long as that shape functions to achieve the teledioptic effect discussed above without providing refractive power (except for the high minus portions). Also, the high minus portions need not be at the center of the supplemental intraocular lens, but can be at any suitable location on the lens. Furthermore, as shown in FIGS. 9 and 10, the supplemental intraocular lens according to the present invention can include pair of haptics for securing the supplemental intraocular lens into the eye. In the example shown in FIGS. 9 and 10, the supplemental intraocular lens is a bi-concave supplemental intraocular lens 116 having a pair of haptics 138 and 140, which are made of a suitable material such as surgical steel or the like. However, a supplemental intraocular lens having any of the shapes described above can include haptics for mounting into the eye 100.

Figure 11:
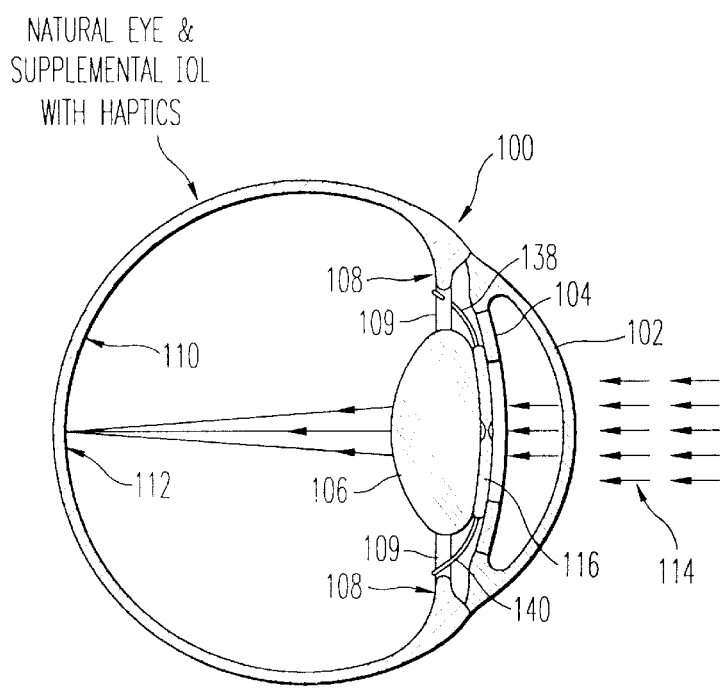
FIG. 11 is a cross-sectional view of an eye showing the relationship between the natural lens of the eye and a bi-concave supplemental intraocular lens having haptics as shown in FIGS. 9 and 10, which has been implanted in the eye.

As shown in FIGS. 11 and 12, the supplemental intraocular lens 116 is placed over or proximate to the natural lens 106 of the eye, and the haptics 138 and 140 are attached, for example, to the zonular ligament 109 of the eye. The haptics 138 and 140 therefore secure the supplemental intraocular lens 116 at the front of the natural lens 106 without the need for an adhesive. The supplemental intraocular lens 116 can then be used in the manner described above with or without a spectacle lens 122 to provide unmagnified, unrestricted vision or magnified and peripherally restricted vision.

The supplemental intraocular lenses are described above as being used with the natural lens of the eye. However, all of the supplemental intraocular lenses described above can be used with an intraocular lens that has already been implanted in the eye to create a modified lens system having the teledioptic features described above.

FIGS. 13 and 14 are front and side schematic views, respectively, of an intraocular lens 142 that is implantable in the eye in place of the natural lens of the eye. In this example, intraocular lens 142 has a bi-convex lens 144 to which are attached haptics 146 and 148 which secure the intraocular lens 142 inside the eye.

As is commonly known in the art, the intraocular lens 142 can include a lens having any desirable shape. For example, as shown in FIG. 15, intraocular lens 150 includes a plano-convex lens 152, and haptics 154 and 156 which are attached to the plano-convex lens 152. Alternatively, as shown in FIG. 16, the intraocular lens 158 includes a concave-convex lens 160 to which are attached haptics 162 and 164. Although not specifically shown, the intraocular lens can be bi-concave, or have any other suitable shapes as known in the art.

FIG. 17 is a cross-sectional view of an eye 100 into which has been mounted an intraocular lens. As known in the art, the natural lens 106 (see FIG. 1) can be removed by making an incision in the eye 100 with a microkeratome, scalpel, laser or any other suitable instrument. The natural lens 106 can then be removed through the incision, and the intraocular lens inserted through the incision and mounted in the eye. In this example, the intraocular lens is shown as intraocular lens 142 which includes a bi-convex lens 142. However, the intraocular lens can have any of the shapes described above.

As illustrated, the eye 100 includes a cornea 102, ciliary sulcus 108, retina 110 and macula 112. The lens 106 has been removed, along with all or substantially all of the zonular ligament 109 (see FIG. 1), and has been replaced with intraocular lens 142. The haptics 146 and 148 are secured to the ciliary sulcus 108 of the eye to secure the bi-convex lens 144 at the appropriate location with respect to the iris 104 and cornea 102. Accordingly, the intraocular lens 142 and cornea 102 function as a lens system which focuses light rays 114 onto the macula 112.

Figure 18:
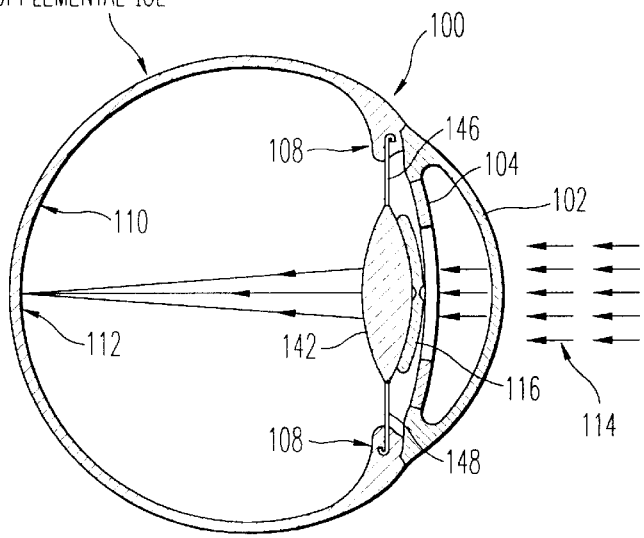
FIG. 18 is a cross-sectional view of an eye into which is implanted a bi-convex intraocular lens, and which further includes a supplemental bi-concave intraocular lens, as shown in FIG. 2 which has been attached to the existing intraocular lens.
Figure 19:
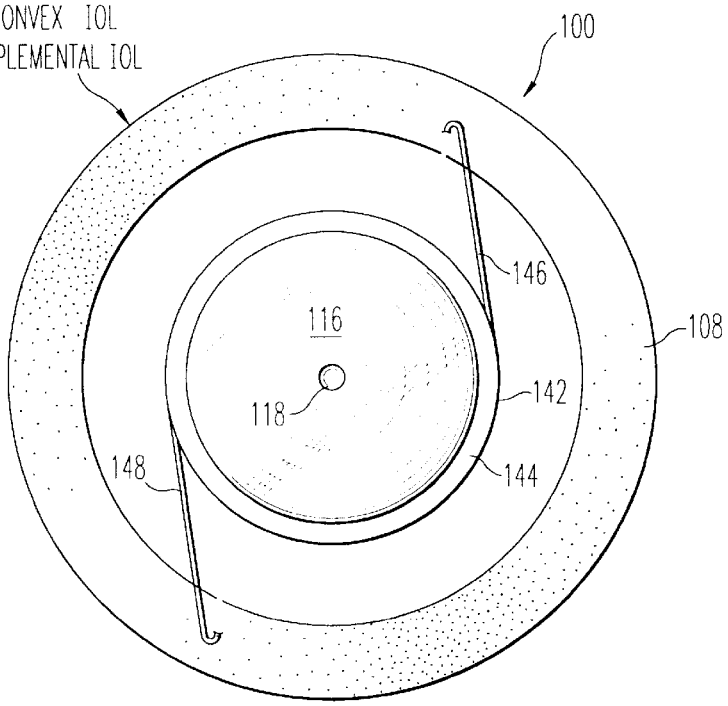
FIG. 19 is a cross-sectional view taken through the eye directly behind the iris to further illustrate the bi-concave supplemental intraocular lens as positioned on an existing bi-convex intraocular lens in the eye as shown in FIG. 18.
Figure 20:
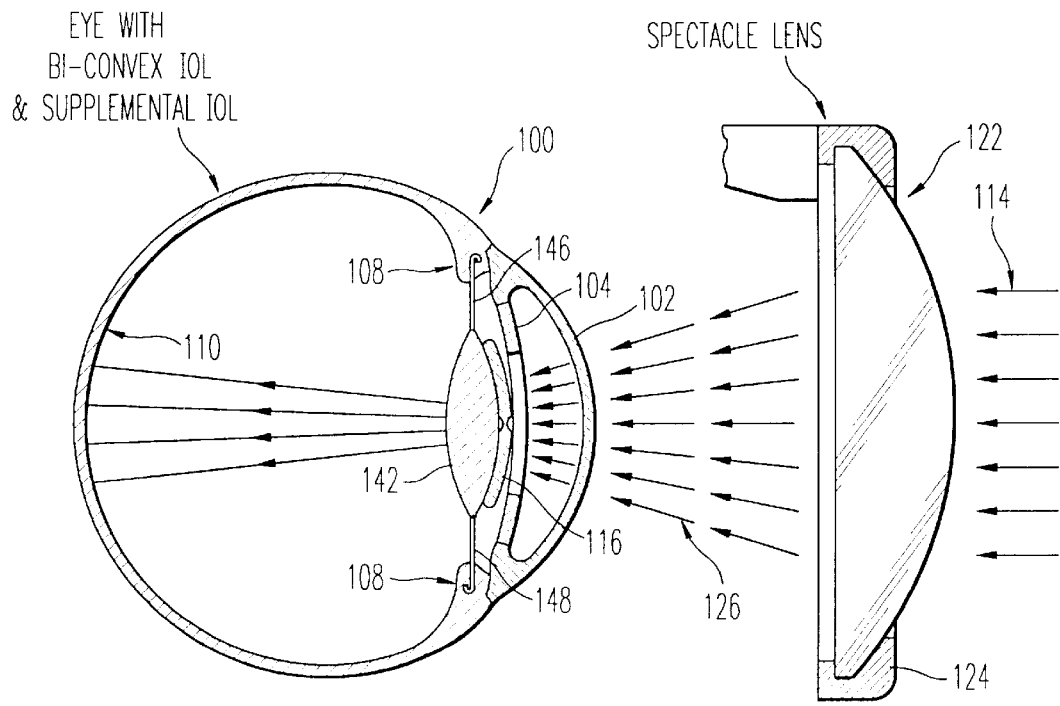
FIG. 20 is a cross-sectional view of the eye as shown in FIG. 18, further illustrating a cross-section of a spectacle lens placed in front of the cornea of the eye.
Figure 21:
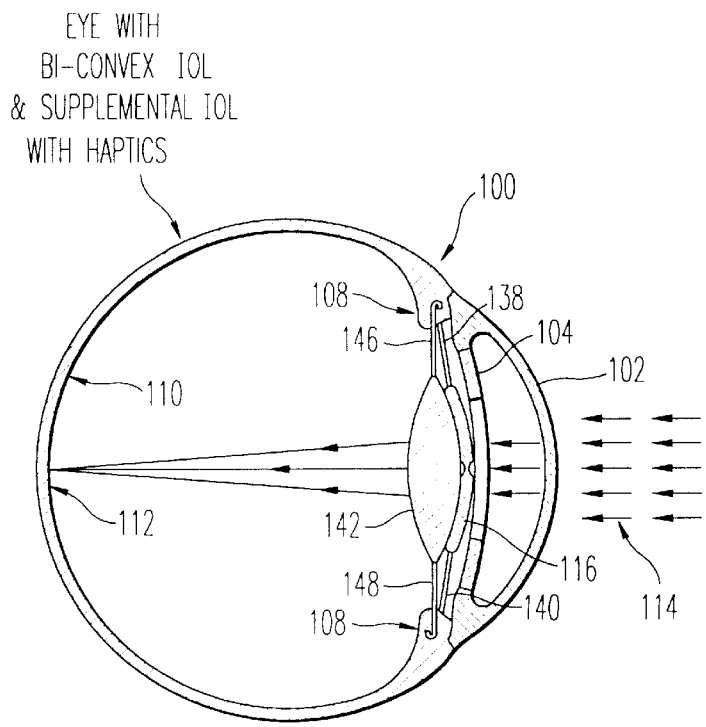
FIG. 21 is a cross-sectional view of the supplemental intraocular lens having haptics as shown in FIGS. 9 and 10, implanted on an existing bi-convex intraocular lens.
Figure 22:
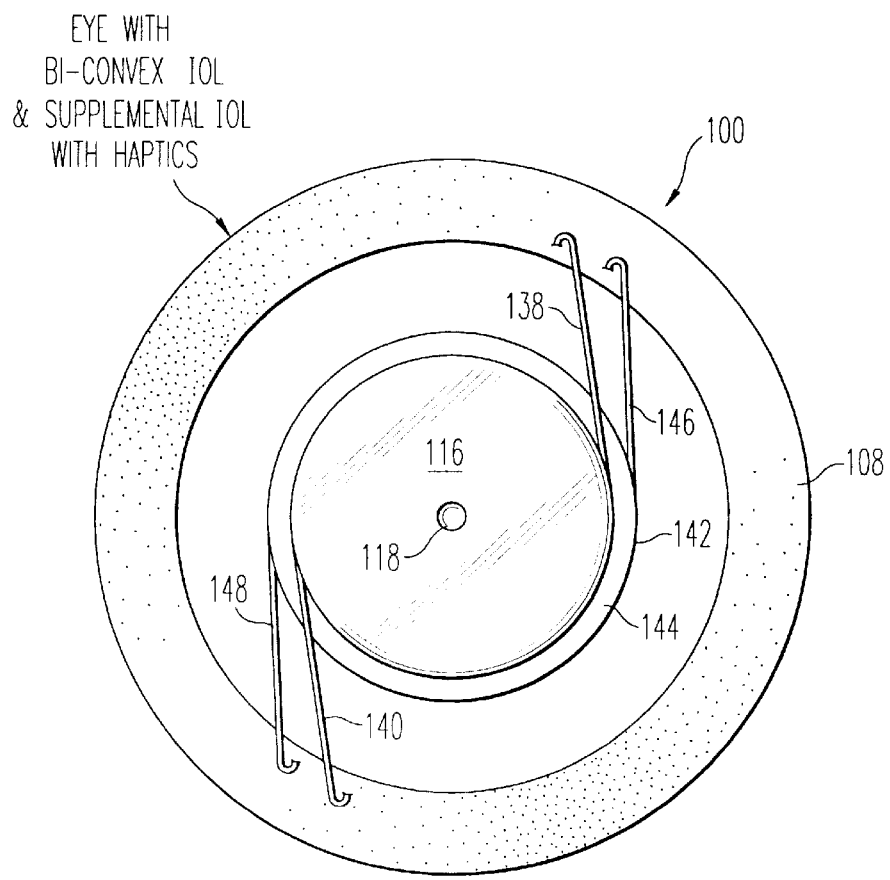
FIG. 22 is a cross-sectional view taken through the eye directly behind the iris to further illustrate the supplemental intraocular lens as positioned on an existing bi-convex intraocular lens as shown in FIG. 21.

As illustrated in FIGS. 18 and 19, the supplemental intraocular lens 116, for example, can be attached to the front surface of the intraocular lens 142 by glue or any other suitable adhesive. Hence, in a manner similar to that described above with regard to the cornea 102, natural lens 106 and supplemental intraocular lens 116, the cornea 102, supplemental intraocular lens 116 and the intraocular lens 142 function as a lens system which focuses light rays 114 onto the retina 110. Also, as shown in FIG. 20, spectacle lens 122 can be placed in front of the eye 100 so that the spectacle lens 122, cornea 102, supplemental intraocular lens 116 and intraocular lens 142 act as a lens system which creates a magnified image on the retina 110. Furthermore, as shown in FIGS. 21 and 22, the supplemental intraocular lens 116 having haptics 138 and 140 as shown in FIG. 9 can be implanted in front of the intraocular lens 142 to eliminate the use of adhesive for securing the supplemental intraocular lens 116 onto or proximate to the intraocular lens 142.

Figure 23:
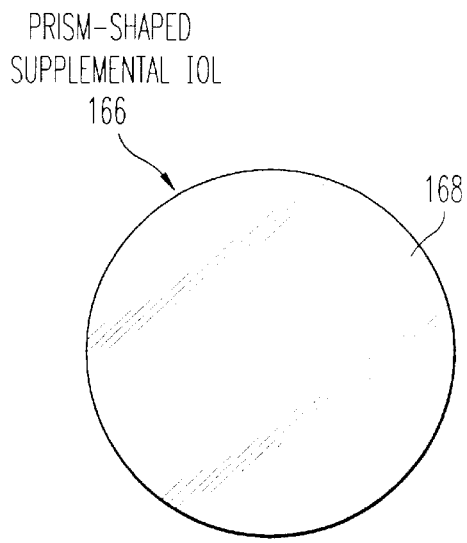
FIG. 23 is a front view of an example of a substantially non-refractive prism-shaped supplemental intraocular lens according to an embodiment of the present invention.
Figure 24:
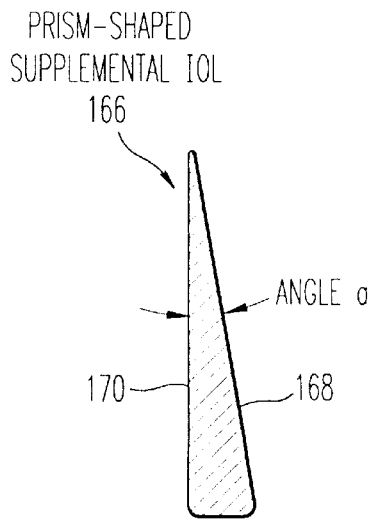
FIG. 24 is a cross-sectional view of the prism-shaped supplemental intraocular lens as shown in FIG. 23.

The supplemental intraocular lens also can be shaped as a prism as shown in FIGS. 23 and 24. That is, supplemental intraocular lens 166 has front and rear surfaces 168 and 170, respectively, which are circular or substantially circular in shape having a diameter ranging between about 3 mm and about 10 mm. However, the surfaces 168 and 170 can be oval or any other suitable shape, and the diameters can be any suitable size. The supplemental intraocular lens 166 has no or substantially no refractive power. As shown explicitly in FIG. 24, front and rear surfaces 168 and 170 do not extend parallel or substantially parallel to each other. Rather, front surface 168 extends at an angle "a" with respect to rear surface 170. The angle "a" can be any practical angle. Hence, as shown in FIG. 24, supplemental intraocular lens 166 has a prism-like cross-sectional shape.

However, the supplemental intraocular lens 166 need not have a prism-shaped cross section, but rather, could have any suitable shape which does not provide any refractive power but diffracts the light rays in the manner described below. That is, the lens 166 can have multiple grooves similar to a fresnel lens, or have steps or lines across its surface which diffract the light rays.

Figure 25:
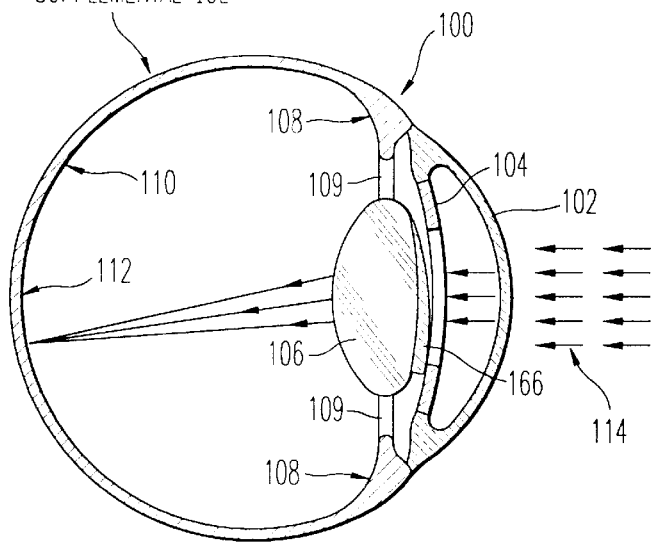
FIG. 25 is a cross-sectional view of an eye illustrating the supplemental prism-shaped intraocular lens as shown in FIGS. 23 and 24 being positioned on a natural lens in the eye.
Figure 26:
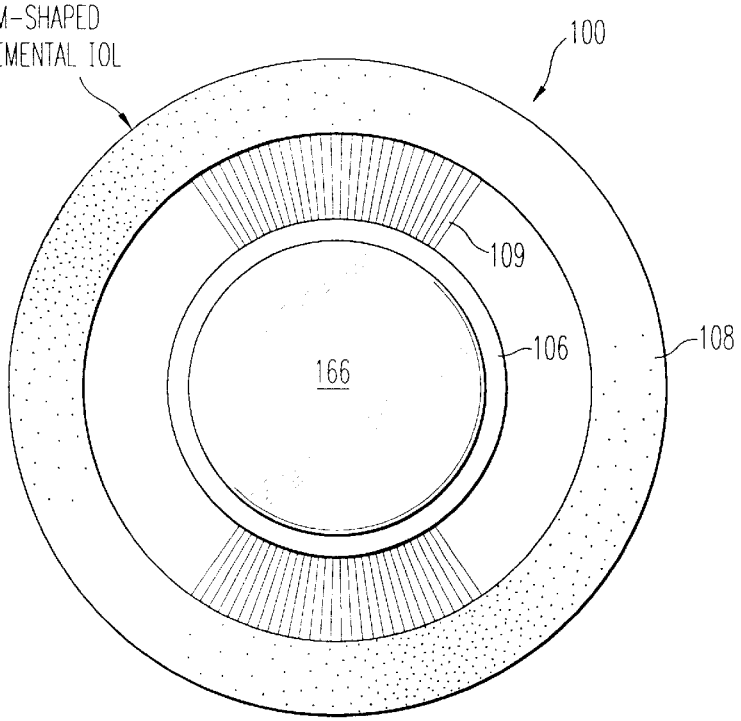
FIG. 26 is a cross-sectional view taken through the eye directly behind the iris to further illustrate the prism-shaped supplemental intraocular lens as positioned on the natural lens of the eye as shown in FIG. 25.

Supplemental intraocular lens 166 can be implanted onto natural lens 106 as shown in FIGS. 25 and 26. That is, supplemental intraocular lens 166 can be attached to the front of natural lens 106 by glue or any other suitable adhesive in a manner similar to that in which supplemental intraocular lens 116 described above is attached to natural lens 106. As shown in FIG. 25 specifically, supplemental intraocular lens 166 acts in conjunction with cornea 102 and natural lens 106 to create a prismatic lens system which focuses light rays 114 onto a portion of the retina 110 away from the macula 112. Because the light rays are focused on to a healthy portion of the retina 110, the image seen by the person is not adversely affected by the macula 112 that has been damaged due to macula degeneration. Accordingly, vision is greatly improved.

Figure 27:
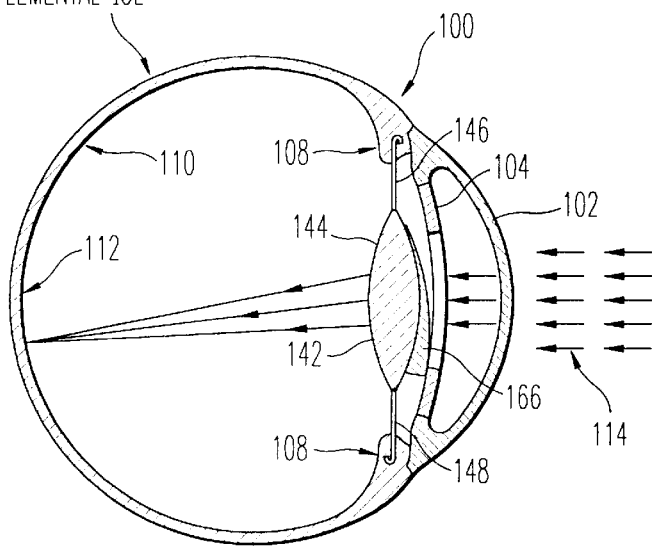
FIG. 27 is a cross-sectional view of an eye having a bi-convex intraocular lens implanted therein, and further having a prism-shaped supplemental intraocular lens as shown in FIGS. 23 and 24 mounted on the bi-convex intraocular lens.
Figure 28:
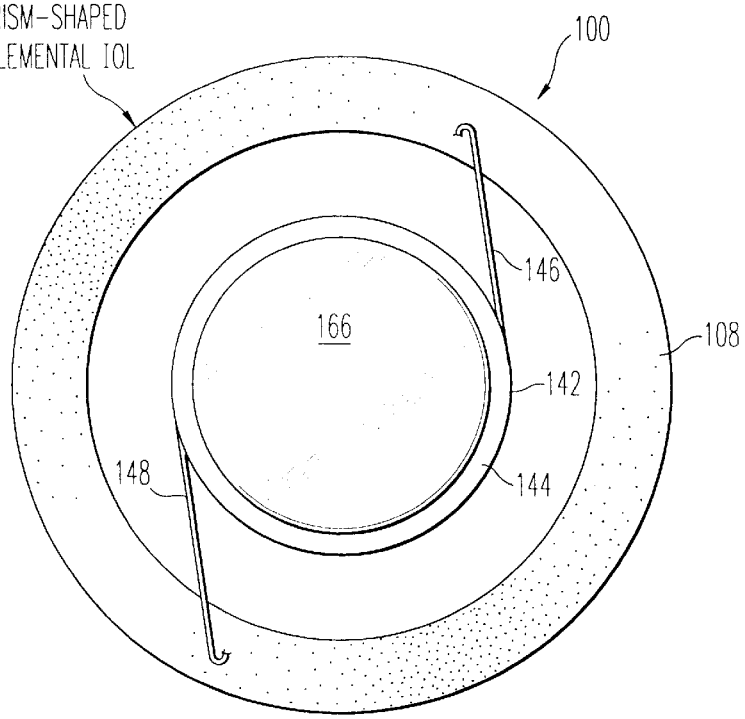
FIG. 28 is a cross-sectional view taken through the eye directly behind the iris to further illustrate the prism-shaped supplemental intraocular lens positioned on the bi-convex intraocular lens in the eye as shown in FIG. 27.
Figure 29:
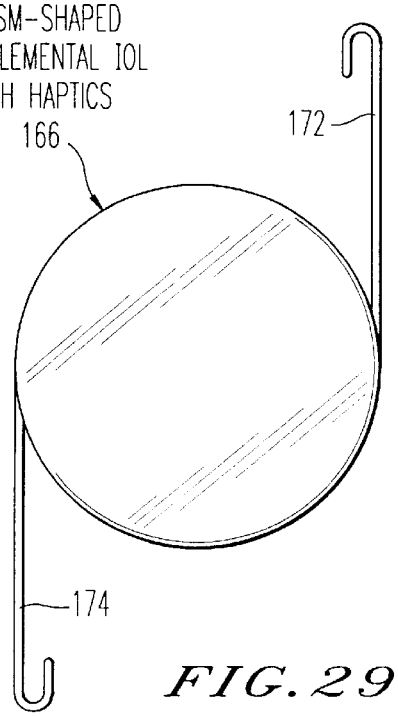
FIG. 29 is a front view showing a prism-shaped supplemental intraocular lens having a plurality of haptics.
Figure 30:
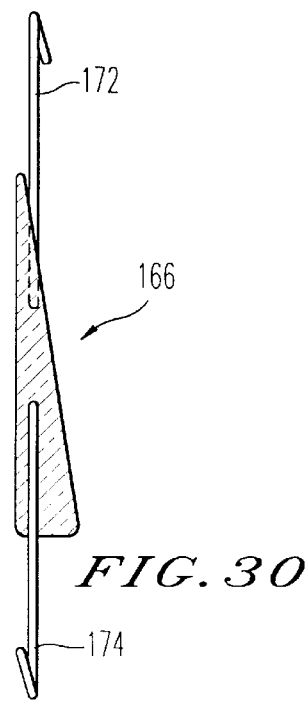
FIG. 30 is a cross-sectional view of the prism-shaped supplemental intraocular lens as shown in FIG. 29.
Figure 31:
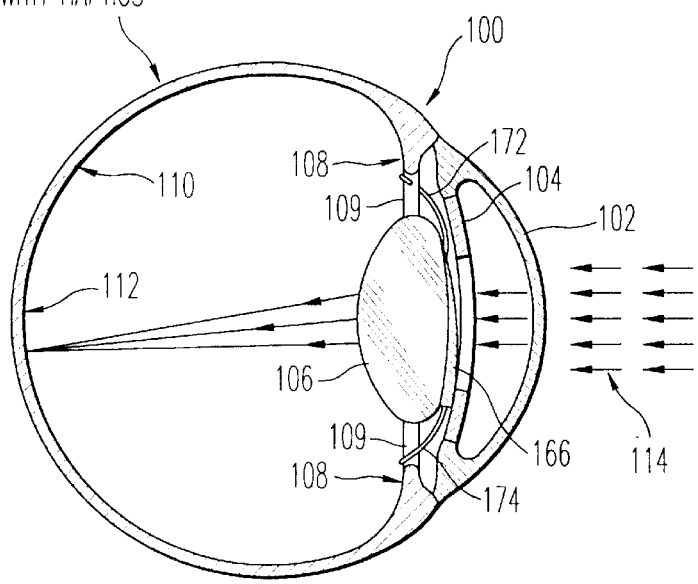
FIG. 31 is a cross-sectional view of an eye having a supplemental prism-shaped intraocular lens with haptics as shown in FIGS. 29 and 30 mounted to the natural lens of the eye.
Figure 32:
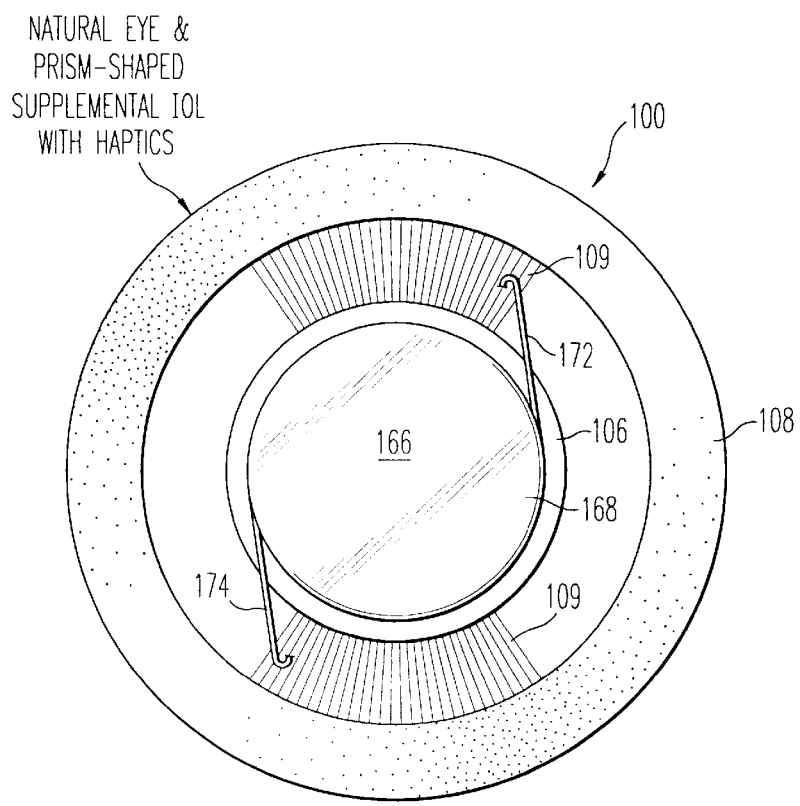
FIG. 32 is a cross-sectional view taken through the eye directly behind the iris to further illustrate the supplemental prism-shaped intraocular lens having haptics which has been inserted onto the natural lens of the eye as shown in FIG. 31.
Figure 33:
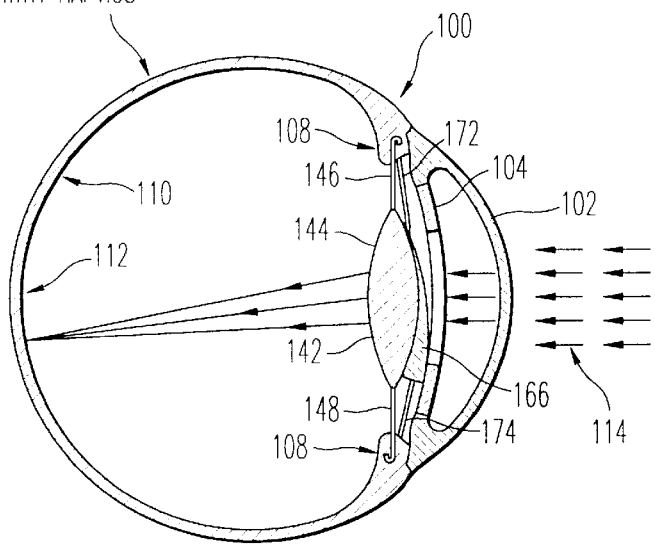
FIG. 33 is a cross-sectional view of an eye having a supplemental intraocular lens with haptics shown in FIGS. 29 and 30 mounted on a bi-convex intraocular lens already positioned in the eye.
Figure 34:
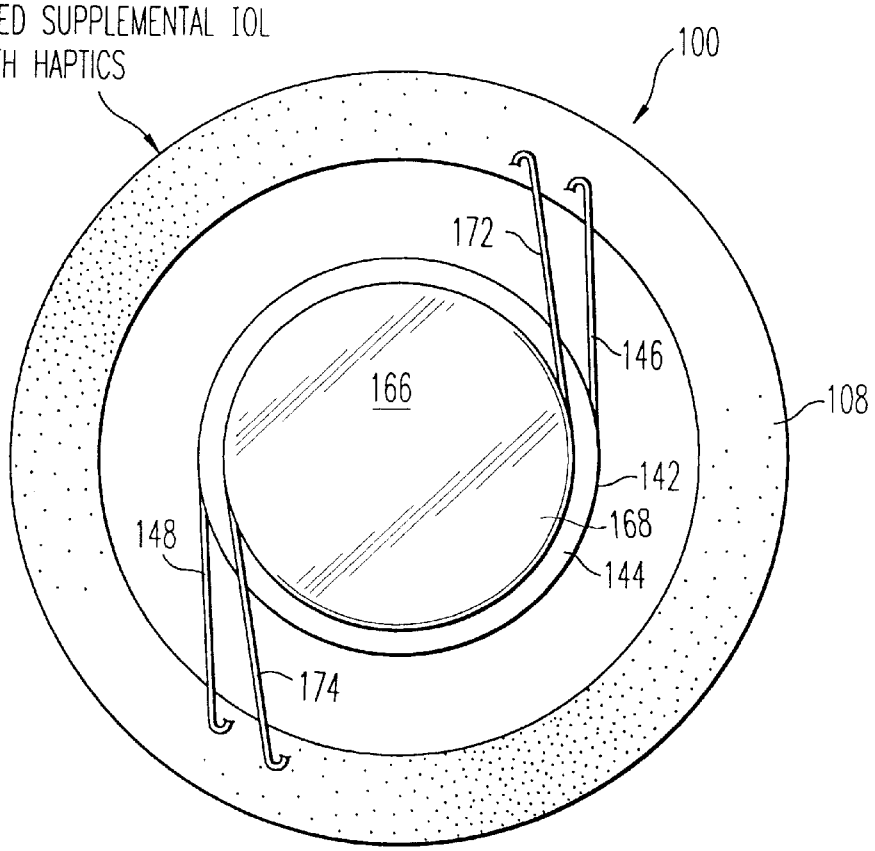
FIG. 34 is a cross-sectional view of the eye taken directly behind the iris to further illustrate the supplemental prism-shaped intraocular lens with haptics mounted on the bi-convex intraocular lens as shown in FIG. 33.

Supplemental intraocular lens 166 can also include the modifications discussed above with regard to supplemental intraocular lens 116. As shown in FIGS. 27 and 28, the supplemental intraocular lens 166 can be attached to an intraocular lens 142 that has been mounted in the eye in place of the natural lens 106. Supplemental intraocular lens 166 also can include haptics 172 and 174 as shown in FIGS. 29 and 30. As shown in FIGS. 31 and 32, the haptics 172 and 174 can be secured, for example, to the zonular ligament 109 or the ciliary sulcus 108 to secure the supplemental intraocular lens 166 onto or proximate to the front of the natural lens 106 without the use of glue or adhesive. Also, as shown in FIGS. 33 and 34, the supplemental intraocular lens 166 with haptics 172 and 174 can be mounted in front of an intraocular lens 142 already implanted in the eye 100.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An intraocular lens, adaptable for implantation in an eye, for modifying the lens system of the eye comprising the cornea of the eye and a natural or artificial lens in the eye, the intraocular lens comprising:
   a lens portion, being configured for implantation into the eye at a location relative to the locations of the cornea and the natural or artificial lens in the eye, the lens portion comprising:
      a first portion having substantially no refractive power; and
      a second portion, adapted to alter a path of light rays passing therethrough to provide the eye with magnified vision when the light rays pass through a lens external of the eye before passing through the second portion.

2. An intraocular lens as claimed in claim 1, wherein:
   the second portion is a minus lens having a power within the range of about −30 to about −120 diopters.

3. An intraocular lens as claimed in claim 1, wherein:
   the first portion permits the light rays to pass therethrough essentially without altering a direction of propagation of the light rays.

4. An intraocular lens as claimed in claim 1, wherein:
   the second portion causes the light rays passing therethrough to diverge.

5. An intraocular lens as claimed in claim 1, further comprising:
   a fastener, coupled to the lens portion and being adaptable to removably secure the lens portion in the eye.

6. An intraocular lens as claimed in claim 5, wherein:
   the fastener comprises an adhesive, adaptable to secure a surface of the lens portion to a surface of the natural or artificial lens in the eye.

7. An intraocular lens as claimed in claim 5, wherein:
   the fastener comprises at least one haptic, coupled to the lens portion and being adaptable to removably secure the intraocular lens in the eye.

8. An intraocular lens as claimed in claim 1, wherein:
   the lens portion comprises at least one of a transparent organic material and a transparent synthetic material.

9. An intraocular lens as claimed in claim 1, wherein:
   the second portion is a bi-concave lens.

10. An intraocular lens as claimed in claim 1, wherein:
    the second portion is a plano-concave lens.

11. An intraocular lens, adaptable for implantation in an eye, for modifying the lens system of the eye comprising the cornea of the eye and a natural or artificial lens in the eye, the intraocular lens comprising:
    a lens portion which has substantially no refractive power and diffracts light passing therethrough, and is adapted for implantation in the eye at a location relative to the locations of the cornea and the natural or artificial lens in the eye to modify the lens system of the eye such that the modified lens system directs light rays passing therethrough onto an area on the retina of the eye other than an area onto which the light rays are directed by the lens system absent the intraocular lens.

12. An intraocular lens as claimed in claim 11, wherein:
    the lens portion is prism-shaped.

13. An intraocular lens as claimed in claim 12, wherein:
    the prism-shaped lens portion comprises a first substantially planar surface and a second substantially planar surface, opposite to the first substantially planar surface and extending at an angle other than 0° with respect to the first substantially planar surface, such that light rays entering the prism through the first surface at a first angle relative to the first surface exits the second surface at a second angle, relative to the first surface, which is different from the first angle.

14. An intraocular lens as claimed in claim 11, wherein:
    the lens portion is fresnel-shaped.

15. An intraocular lens as claimed in claim 11, further comprising:
    a fastener, coupled to the lens portion and being adaptable to removably secure the lens portion in the eye.

16. An intraocular lens as claimed in claim 15, wherein:
    the fastener comprises an adhesive, adaptable to secure a second surface of the lens portion to a surface of the natural or artificial lens in the eye.

17. An intraocular lens as claimed in claim 15, wherein:

the fastener comprises at least one haptic, coupled to the lens portion and being adaptable to removably secure the intraocular lens in the eye.

18. An intraocular lens as claimed in claim 11, wherein:

the lens portion comprises at least one of a transparent organic material and a transparent synthetic material.

19. A method for modifying a lens system of the eye comprising the cornea of the eye and a natural or artificial lens in the eye, the method comprising the steps of:

providing an intraocular lens comprising a first portion which is substantially non-refractive and a second portion; and implanting the intraocular lens into the eye at a location relative to the locations of the cornea and the natural or artificial lens in the eye to modify the lens system of the eye such that the second portion is positioned to alter a path of light rays passing therethrough to provide the eye with magnified vision when the light rays pass through a lens external of the eye before passing through the second portion.

20. A method as claimed in claim 19, further comprising the step of:

placing the external lens at a location outside the eye such that the light rays pass through the external lens before entering the eye.

21. A method as claimed in claim 19, further comprising the step of:

securing the intraocular lens to a surface of the natural or artificial lens in the eye.

22. A method as claimed in claim 19, further comprising the step of:

securing the intraocular lens to a portion of the eye other than the natural or artificial lens in the eye.

23. A method for modifying a lens system of the eye comprising the cornea of the eye and a natural or artificial lens in the eye, the method comprising the steps of:

providing an intraocular lens comprising a substantially non-refractive portion which diffracts light passing therethrough; and implanting the intraocular lens in the eye at a location relative to the locations of the cornea and the natural or artificial lens in the eye to modify the lens system of the eye such that the modified lens system directs light rays passing therethrough onto an area on the retina of the eye other than an area onto which the light rays are directed by the lens system absent the intraocular lens.

24. A method as claimed in claim 23, further comprising the step of:

securing the intraocular lens to a surface of the natural or artificial lens in the eye.

25. A method as claimed in claim 23, further comprising the step of:

securing the intraocular lens to a portion of the eye other than the natural or artificial lens in the eye.

26. An intraocular lens, adaptable for implantation in an eye, for modifying a lens system of the eye comprising the cornea of the eye and a natural or artificial lens in the eye, the intraocular lens comprising:

a substantially non-refractive portion which permits passage of light rays therethrough without altering a path of propagation of the light rays, the substantially non-refractive portion including a portion, adapted to alter a path of propagation of the light rays passing therethrough to alter the lens system of the eye to direct light rays passing therethrough onto an area on the retina of the eye other than an area onto which the light rays are directed by the lens system absent the intraocular lens.

27. An intraocular lens as claimed in claim 26, wherein:

the portion alters the path of propagation of the light rays when the light rays pass through an external lens before passing into the eye.

28. A method for modifying a lens system of the eye comprising the cornea of the eye and a natural or artificial lens in the eye, the method comprising the steps of:

providing a substantially non-refractive intraocular lens comprising a portion which alters a direction of propagation of light rays passing therethrough; and implanting the intraocular lens in the eye at a location relative to the locations of the cornea and the natural or artificial lens in the eye to modify the lens system of the eye such that the modified lens system directs light rays passing therethrough onto an area on the retina of the eye other than an area onto which the light rays are directed by the lens system absent the intraocular lens.

29. A method as claimed in claim 28, further comprising the step of:

positioning a lens external of the eye such that the light rays pass through the external lens before entering the eye;

and wherein said portion alters the direction of propagation of the light rays which have passed through the external lens.

30. A method as claimed in claim 28, further comprising the steps of:

checking the vision of the eye having the intraocular lens implanted therein;

if the vision is less than a desired vision, performing the following steps:

removing the intraocular lens from the eye;

implanting a second substantially non-refractive intraocular lens in the eye, the second intraocular lens having a second portion which alters a direction of propagation of light passing therethrough; and checking the vision of the eye having the second intraocular lens implanted therein.

\* \* \* \* \*